United States Patent
Durand

(10) Patent No.: US 10,542,904 B2
(45) Date of Patent: Jan. 28, 2020

(54) SYSTEMS AND METHODS FOR AT HOME NEURAL RECORDING

(71) Applicant: Case Western Reserve University, Cleveland, OH (US)

(72) Inventor: Dominique M. Durand, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 336 days.

(21) Appl. No.: 15/392,043

(22) Filed: Dec. 28, 2016

(65) Prior Publication Data
US 2017/0112408 A1    Apr. 27, 2017

Related U.S. Application Data

(63) Continuation-in-part of application No. 14/683,197, filed on Apr. 10, 2015, now Pat. No. 9,955,907.
(Continued)

(51) Int. Cl.
*A61B 5/0478* (2006.01)
*A61B 5/0476* (2006.01)
(Continued)

(52) U.S. Cl.
CPC .......... *A61B 5/0478* (2013.01); *A61B 5/0006* (2013.01); *A61B 5/04012* (2013.01);
(Continued)

(58) Field of Classification Search
CPC . A61B 5/0478; A61B 5/0006; A61B 5/04012; A61B 5/0476; A61B 5/04842;
(Continued)

(56) References Cited

U.S. PATENT DOCUMENTS

| | | | | |
|---|---|---|---|---|
| 5,813,993 A | * | 9/1998 | Kaplan | A61B 5/0476 600/26 |
| 6,301,493 B1 | * | 10/2001 | Marro | A61B 5/0478 600/383 |

(Continued)

OTHER PUBLICATIONS

Couturier, N. et al., (2013). Auditive and visual sensorial stimulation is able to suppress seizure frequency in two animal models of epilepsy. (manuscript in preparation).
(Continued)

Primary Examiner — Navin Natnithithadha
(74) Attorney, Agent, or Firm — Tarolli, Sundheim, Covell & Tummino LLP

(57) ABSTRACT

One aspect of the present disclosure relates to a system to facilitate at home neural monitoring. The system can include a wearable device and an external device. The wearable device can include an electrode configured to be placed behind a patient's ear to record an electroencephalogram (EEG) signal; an amplifier to amplify the EEG signal; a battery; and a wireless transmission system to transmit the amplified EEG signal. The external device can be configured to receive the amplified EEG signal and to perform analysis of the amplified EEG signal. In some instances, the external device can also provide neural stimulation (e.g., acoustic, visual, or electrical) to the wearable device in response to analysis of the amplified EEG signal.

15 Claims, 3 Drawing Sheets

Related U.S. Application Data

(60) Provisional application No. 61/983,105, filed on Apr. 23, 2014, provisional application No. 62/271,592, filed on Dec. 28, 2015.

(51) Int. Cl.
  *A61N 1/20* (2006.01)
  *A61B 5/00* (2006.01)
  *A61B 5/04* (2006.01)
  *A61N 1/36* (2006.01)
  *A61N 1/04* (2006.01)

(52) U.S. Cl.
  CPC .......... *A61B 5/4094* (2013.01); *A61B 5/4836* (2013.01); *A61B 5/6803* (2013.01); *A61N 1/0456* (2013.01); *A61N 1/20* (2013.01); *A61N 1/36025* (2013.01)

(58) Field of Classification Search
  CPC . A61B 5/04845; A61B 5/4094; A61B 5/4812; A61B 5/4836; A61B 5/6803; A61B 5/6898; A61B 5/7225; A61B 5/0015; A61B 5/165; A61B 5/4824; A61B 5/4845; A61B 5/7203; A61B 5/725; A61B 2560/0468; A61B 2562/04; A61M 21/00; A61M 2021/0022; A61M 2021/0027; A61M 2021/0044; A61M 2021/0072; A61M 2205/3553; A61M 2205/3561; A61M 2205/3569; A61M 2205/3584; A61M 2205/3592; A61M 2205/8206; A61M 2209/088; A61M 2230/10; A61N 1/0456; A61N 1/20; A61N 1/36025; A61N 5/0622; A61N 2005/0647; A61N 2005/0648
  USPC .................................................. 600/544–545
  See application file for complete search history.

(56) References Cited

U.S. PATENT DOCUMENTS

| | | | |
|---|---|---|---|
| 6,591,138 B1 | 7/2003 | Fischell et al. | |
| 8,027,737 B2* | 9/2011 | Kokones | A61N 1/0529 607/115 |
| 8,271,075 B2* | 9/2012 | Chuang | A61B 5/0478 600/383 |
| 8,676,342 B2* | 3/2014 | Kokones | A61N 1/0529 607/115 |
| 8,781,570 B2* | 7/2014 | Chuang | A61B 5/0478 381/74 |
| 8,914,100 B2* | 12/2014 | Adachi | A61B 5/048 600/544 |
| 8,938,301 B2* | 1/2015 | Hagedorn | A61B 5/0478 607/45 |
| 9,144,405 B2* | 9/2015 | Kim | A61B 5/743 |
| 9,392,956 B2* | 7/2016 | Luo | A61B 5/0478 |
| 9,618,749 B2* | 4/2017 | Deleeuw | H04N 13/398 |
| 9,788,747 B2* | 10/2017 | Hagedorn | A61B 5/0478 |
| 9,808,199 B2* | 11/2017 | Kilsgaard | A61B 5/0476 |
| 9,814,426 B2* | 11/2017 | Connor | A61B 5/0476 |
| 9,918,650 B2* | 3/2018 | Kilsgaard | A61B 5/0478 |
| 9,955,907 B2* | 5/2018 | Durand | A61B 5/04842 |
| 9,968,297 B2* | 5/2018 | Connor | A61B 5/6803 |
| 10,045,718 B2* | 8/2018 | Yang | A61B 5/1171 |
| 10,178,969 B2* | 1/2019 | Anwar | A61B 5/165 |
| 2009/0054802 A1* | 2/2009 | Kuo | A61B 5/0408 600/545 |
| 2009/0214060 A1* | 8/2009 | Chuang | A61B 5/0478 381/151 |
| 2011/0307031 A1* | 12/2011 | Kokones | A61N 1/0529 607/45 |
| 2012/0029336 A1* | 2/2012 | Terada | A61B 5/04004 600/383 |
| 2012/0191000 A1* | 7/2012 | Adachi | A61B 5/048 600/544 |
| 2012/0316418 A1* | 12/2012 | Kilsgaard | A61B 5/0476 600/379 |
| 2013/0039509 A1* | 2/2013 | Chuang | A61B 5/0478 381/74 |
| 2013/0296731 A1* | 11/2013 | Kidmose | A61B 5/04845 600/544 |
| 2014/0159862 A1* | 6/2014 | Yang | A61B 5/1171 340/5.52 |
| 2014/0171775 A1* | 6/2014 | Kilsgaard | A61B 5/0478 600/379 |
| 2014/0350431 A1* | 11/2014 | Hagedorn | A61B 5/0478 600/544 |
| 2015/0305667 A1* | 10/2015 | Durand | A61B 5/04842 600/27 |
| 2015/0313496 A1* | 11/2015 | Connor | A61B 5/0476 600/301 |
| 2016/0178904 A1* | 6/2016 | Deleeuw | H04N 13/398 345/8 |
| 2016/0256086 A1* | 9/2016 | Byrd | A61B 5/0059 |
| 2016/0367204 A1* | 12/2016 | Won | A61B 5/747 |
| 2017/0020454 A1* | 1/2017 | Keteyian | A61B 5/6803 |
| 2017/0027467 A1* | 2/2017 | Hagedorn | A61B 5/0478 |
| 2017/0041699 A1* | 2/2017 | Mackellar | H04R 1/1075 |
| 2017/0185149 A1* | 6/2017 | Oluwafemi | G06F 3/015 |
| 2017/0188947 A1* | 7/2017 | Connor | A61B 5/6803 |
| 2018/0035939 A1* | 2/2018 | Durand | A61B 5/04842 |

OTHER PUBLICATIONS

Hughes, J. R. et al., ""The Mozart effect" on epileptiform activity." Clinical Electroencephalography 29.3 (1998): 109-119.

Kile et al., "Low frequency stimulation decreases seizure activity in a mutation model of epilepsy," Epilepsia 51.9 (2010): 1745-1753.

Koubeissi et al., "Low Frequency Electrical Stimulation of White Matter Tracts in Intractable Mesial Temporal Lobe Epilepsy (IN5-1.010)." Neurology 78.1 Supplement (2012): IN5-1.

Lerner, Y. et al., "Eyes wide shut: amygdala mediates eyes-closed effect on emotional experience with music." PLoS One 4.7 (2009): e6230.

Lin, L. et al., Mozart K.545 Mimics K.448 in Reducing Epileptiform Discharges in Epileptic Children (2012).

Lin, L. et al., "Mozart K. 448 acts as a potential add-on therapy in children with refractory epilepsy," Epilepsy & Behavior 20.3 (2011): 490-493.

Lin, L, et al., "Mozart K. 448 and epileptiform discharges: effect of ratio of lower to higher harmonics." Epilepsy research 89.2 (2010): 238-245.

Lin, L. et al., "The long-term effect of listening to Mozart K. 448 decreases epileptiform discharges in children with epilepsy." Epilepsy & Behavior 21.4 (2011): 420-424.

Meinecke, F. C. et al., "Measuring phase synchronization of superimposed signals." Physical Review Letters 94.8 (2005): 084102.

Menkes, D. L. et al., "Slow-Frequency Repetitive Transcranial Magnetic Stimulation in a Patient with Focal Cortical Dysplasia." Epilepsia 41.2 (2000): 240-242.

Rashid, S. et al., "Low frequency stimulation of ventral hippocampal commissures reduces seizures in a rat model of chronic temporal lobe epilepsy." Epilepsia 53.1 (2012): 147-156.

\* cited by examiner

SYSTEMS AND METHODS FOR AT HOME NEURAL RECORDING

RELATED APPLICATIONS

This application claims the benefit of U.S. Provisional Application No. 62/271,592, entitled "BERS: BEHIND THE EAR RECORDING AND STIMULATION SYSTEM," filed Dec. 28, 2015. The entirety of this application is hereby incorporated by reference for all purposes.

This application is also a Continuation-in-Part of U.S. application Ser. No. 14/683,197, entitled "Low Frequency Non-Invasive Sensorial Stimulation for Seizure Control," filed Apr. 10, 2015, claiming the benefit of U.S. Provisional Application No. 61/983,105, filed Apr. 23, 2014 (now expired). The entirety these applications is hereby incorporated by reference for all purposes.

TECHNICAL FIELD

The present disclosure relates generally to at home neural recording and, more specifically, to systems and methods for at home neural recording using electrodes that are easily placed at locations that provide a stable signal.

BACKGROUND

Electrical activity of the brain can be recorded using electroencephalography (EEG), an accepted and useful technique for obtaining information about brain activity. The information about brain activity obtained from an EEG recording can be used in the diagnosis and monitoring of sleep disorders, epilepsy, attention deficit disorder, depression, chemical dependency, pain, and other disorders. To ensure accurate EEG recordings through proper electrode placement, EEG tests are generally conducted in a hospital or office setting by a trained medical professional. However, the technology used to record the EEG data, as well as the hospital or office setting, is both uncomfortable and unnatural for the patient, leading to questions of whether the EEG data is truly an accurate reflection of the patient's natural brain activity.

SUMMARY

The present disclosure relates generally to at home neural recording and, more specifically, to systems and methods for at home neural recording using electrodes that are easily placed at locations that produce a stable signal. An example neural recording provided by the systems and methods of the present disclosure that can be performed at home is an electroencephalogram (EEG) recording that can provide data that is a reflection of the patient's natural brain activity.

In an aspect, the present disclosure can include a system to facilitate at home neural monitoring. The system can include a wearable device and an external device. The wearable device can include an electrode configured to be placed behind a patient's ear to record an EEG signal; an amplifier to amplify the EEG signal; a battery; and a wireless transmission system to transmit the amplified EEG signal. The external device can be configured to receive the amplified EEG signal and to perform analysis of the amplified EEG signal.

In another aspect, the present disclosure can include a method for at home neural recording and stimulation. The method can be executed, for example, by a wearable device that can include an electrode configured to be placed behind a patient's ear to record an EEG signal; an amplifier to amplify the EEG signal; a battery; and a wireless transmission system to transmit the amplified EEG signal and receive a stimulation signal. EEG signals can be recorded by electrodes behind a patient's ear. The EEG signals can be sent wirelessly to an external device. A stimulation signal can be received from the eternal device in response to a detection of abnormal brain activity (e.g., seizure activity) based on an analysis of the EEG signals.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
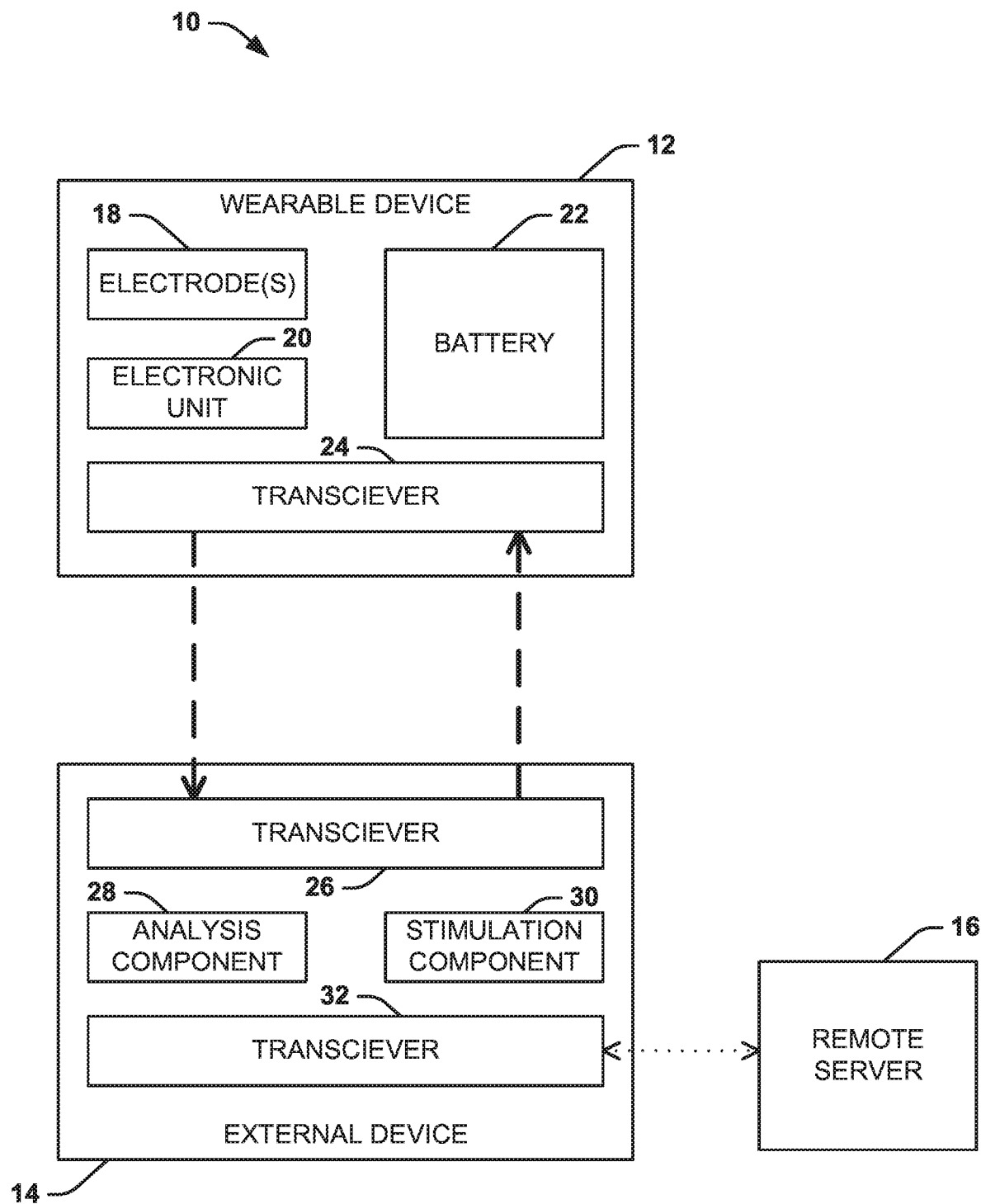
FIG. 1 is a schematic diagram showing a system that can be used for at home neural recording in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "neural recording" can refer to the measurement of electrical activity of one or more neurons. An example type of neural recording is an electroencephalogram (EEG), which can be used in the diagnosis and monitoring of sleep disorders, epilepsy, attention deficit disorder, depression, chemical dependency, pain, and other disorders.

As used herein, the term "at home" neural recording can refer to a neural recording that is administered during a patient's everyday life, rather than at a hospital or other type of office. For example, an at home neural recording can be administered without the need for a trained professional and, instead, can be administered by patients themselves, by the patient's family member, or by the patient's caregiver.

As used herein, the term "stimulation" can refer to modulation of at least a portion of a patient's nervous system. For example, the stimulation can be applied to a portion of the brain and/or one or more spinal cord nerves, such as cervical nerves. The stimulation can be, for example, an electrical stimulation, a vibration, an audio stimulation, and/or a visual stimulation.

As used herein, the term "neural tissue" can refer tissue that is specialized for the conduction of electrical impulses that convey information or instructions from one region of the body to another via one or more nerves. As examples, the neural tissue can include nerves of the peripheral nervous system (e.g., spinal cord nerves, such as cervical nerves), nerves of the central nervous system, or any combination thereof.

As used herein, the term "nerve" can refer to one or more fibers that employ electrical and chemical signals to transmit motor, sensory, and/or autonomic information from one body part to another. A nerve can refer to either a component of the central nervous system or the peripheral nervous system (e.g., spinal cord nerves, such as cervical nerves).

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "non-invasive" can be used to refer a medical procedure not requiring the introduction of instruments into the patient's body.

II. Overview

The present disclosure relates generally to at home neural recordings. Neural recordings can refer to any type of recording or measurement that can provide information about activity of a patient's neural tissue. One type of neural recording is electroencephalogram (EEG), which is an accepted and useful technique to obtain information about the patient's brain activity. Traditionally, the EEG has required a complex placement of recording electrodes by a trained professional and cannot be administered at home. The present disclosure eliminates the need for the trained professional. Indeed, the present disclosure relates more specifically to systems and methods for reliable at home neural recording (like EEG) using electrodes that are easily placed at locations that produce a stable signal. Indeed, the at home neural recording can be non-invasive.

The at home nature of the neural recordings of the present disclosure can provide data that is a reflection of the patient's natural brain activity. The recording electrodes can be part of a wearable device, in a number smaller than that required by a traditional EEG neural recording. The recording electrodes can be specifically positioned within the wearable device, allowing for easy placement of the recording electrodes while wearing the wearable device. The recording electrodes can be placed in a stable position so that the recordings are relatively free of artifacts. The wearable device can communicate with a portable external device, which can be similar in size to a cellular phone or other portable electronic device, to analyze the recorded signal for monitoring and feedback applications. In some instances, the external device can configure a stimulation to be applied to the patient as feedback in response to the recorded signal.

III. Systems

One aspect of the present disclosure can include a system 10 (FIG. 1) that can be used for at home neural recording. The system 10 can include a wearable device 12 that a patient can wear to record a neural signal of the at home neural recording. The wearable device 12 can be in wireless communication with an external device 14 that can be configured to receive the recorded neural signal and to perform analysis of the recorded neural signal. For example, the external device 14 can be a portable device similar in size to a cellular phone or tablet computing device. In some instances, the external device 14 can be in wireless communication with a remote server to transmit information, including the recorded signal and/or the analysis.

For ease of explanation, the system 10 can record electroencephalogram (EEG) signals from an epileptic patient. EEG is a technique that can provide accepted and useful information about a patient's brain activity; however, to ensure accurate EEG recordings through proper electrode placement, EEG tests are generally conducted in a hospital or office setting by a trained medical professional, rather than at home by the patient, family member, or caregiver without specialized training. The system 10, however, does not require specialized training for administration, enabling an at home EEG for an epileptic patient. However, the at home EEG recording can be used for monitoring (and, in some instances, treatment) of other disorders, including: attention deficit disorders, depression, mood disorders, chemical dependency, pain control, or the like.

Figure 2:
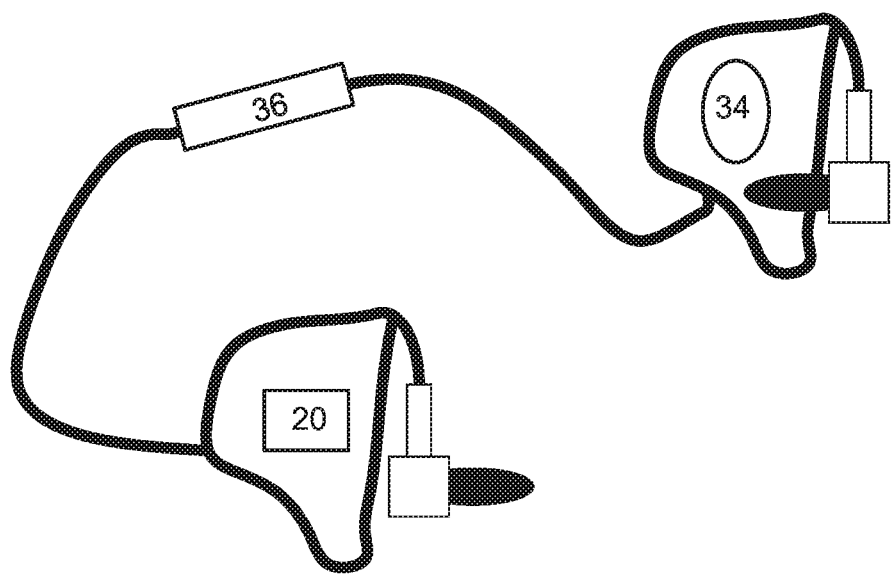
FIGS. 2 and 3 are schematic diagrams illustrating example wearable devices that can be used in connection with the system in FIG. 1.
Figure 3:
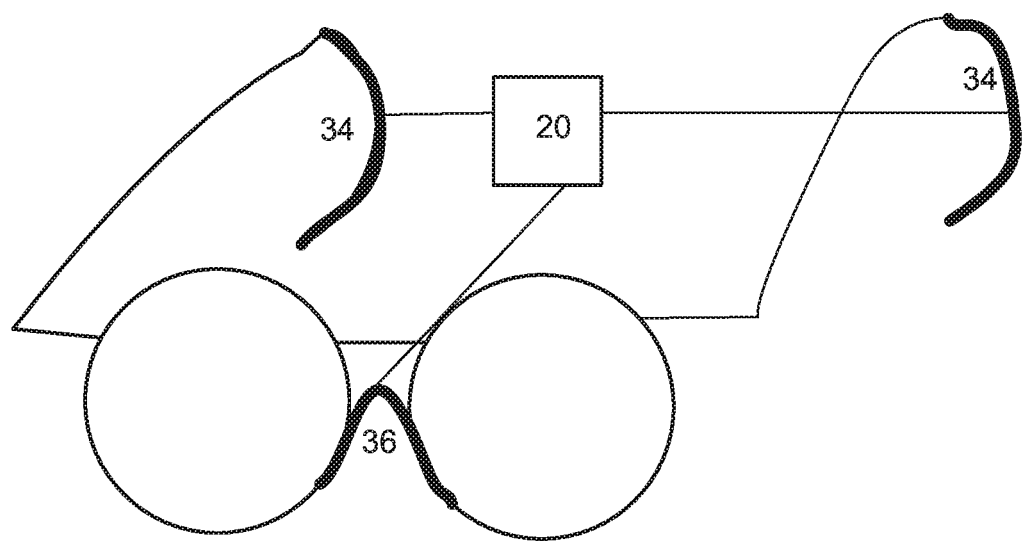

The wearable device 12 can be configured for patient comfort and cosmetic acceptability. For example, the wearable device 12 can be shaped as earphones/headphones (shown in FIG. 2), glasses (shown in FIG. 3), a hat, a headband, a sleep mask, or the like. For example, a sleep mask can be used for overnight recording, while glasses, a hat, or a headband can be used for recording during the day. In another example, headphones can be used for day or overnight recording. In any configuration, the wearable device can include one or more electrodes 18 configured and shaped for the corresponding type of at home neural recording. For at home EEG, the one or more electrodes can be arranged in a portion of the wearable device 12 configured to be placed behind the patient's ears (FIGS. 2 and 3, element 34). As an example, the one or more electrodes 18 can be placed over the mastoid process behind the patient's ear.

The one or more electrodes 18 can refer to one or more recording electrodes. In some instances, the one or more electrodes 18 can also include a reference electrode (FIGS. 2 and 3, element 36) placed remote from the recording electrodes. In other instances, the one or more electrodes 18 can also include one or more stimulating electrodes. However, the one or more recording electrodes can also be configured as stimulating electrodes. In either case, the stimulating electrodes can be low-impedance electrodes. For example, the low-impedance electrodes can be capacitive electrodes.

The one or more electrodes 18 can be in a number smaller than required by traditional EEGs. Additionally, the smaller number of electrodes requires a smaller number of connections. In one example, the one or more electrodes 18 can be configured to be floating electrodes with two recording electrodes and no reference electrode. In another example, the one or more electrodes 18 can include two recording electrodes placed behind the patient's ears and a third reference electrode placed remotely (this example arrangement of the recording electrodes 34 and reference electrode 36 is shown in FIGS. 2 and 3). As a further example, more than two recording electrodes can be used with or without the reference electrode. The one or more electrodes 18 can be applied with or on a conductive gel. In some instances, the conductive gel can be placed behind the patient's ear before placement of the one or more electrodes 18. For example, the wearable device 12 can be configured to release the conductive gel behind the patient's ear.

Notably, the wearable device 12 of the system 10 provides simple placement of the one or more electrodes 18, allowing the untrained patient, family member, or caregiver to administer the EEG to the patient at home. For example, when the wearable device 12 is worn by the patient, the one or more electrodes 18 can be placed in stable positions, allowing recordings to be taken for an extended period of time. For example, the extended period of time can be at least 8 hours (or overnight). As a further example, the extended period of time can be at least 15 hours. As another example, the extended period of time can be at least 24 hours. Additionally, the recording by the one or more electrodes 18 can be relatively free of artifacts. For example, the one or more electrodes 18 can be made of a polymer, such as carbon impregnated silicone, or a conductive wire mesh, such as silver mesh.

To facilitate placement of the one or more electrodes 18 on the patient, the one or more electrodes 18 can be in predefined locations within the wearable device 12. The predefined locations can ensure stable neural recordings by the one or more electrodes 18 when the wearable device 12 is placed on the patient. In some instances, the one or more electrodes 18 of the wearable device 12 can be in positions configured for the dimensions of the specific patient. In other instances, the wearable device 12 can include a plurality of electrodes 18 and only a portion of the plurality of electrodes 18 may be used, depending on the specific patient. For example, the one or more electrodes 18 can be arranged in the wearable device 12 for placement behind one or more of the patient's ears. In this example, the one or more electrodes 18 can record signals from the limbic region of the brain. For example, EEG signals obtained from the limbic region of the brain have been shown to have similar reliability and usability to those obtained by conventional electrodes placed in the temporal area of the brain.

In addition to the one or more electrodes 18, the wearable device 12 can include an electronic unit 20. The electronic unit 20 can include one or more amplifiers to amplify the recorded EEG signals. The electronic unit 20 can also include filter circuitry that filters the recorded EEG signals recorded by the one or more electrodes 18. The electronic unit 20 can also include additional circuitry that can facilitate amplification, filtering or other signal processing of the EEG signals. In some instances, the electronic unit 20 can also include a processing means, like a microprocessor. For example, when two electrodes are used, a differential value (e.g., related to a power spectrum over a frequency range) can be determined from the recorded signals.

Components of the wearable device 12, like the one or more electrodes 18 and/or the electronics unit, can receive power from a battery 22 power source. The battery 22 power source can allow the wearable device 12 to be portable. However, the wearable device 12 may also receive line power via an AC adaptor. For example, the line power may be used when the battery 22 power source requires charging.

The wearable device 12 can also include a transmission means, such as transceiver 24, that can send the recorded signal, which may be amplified and/or filtered, to an external device 14. In some instances, the transceiver 24 can communicate according to a short-range wireless transmission protocol like Bluetooth, Bluetooth Low Energy, ZigBee, or the like. However, the transceiver 24 may communicate according to a longer-range protocol, like WiFi. Additionally, in some instances, the transceiver 24 can provide bidirectional communication with the external device 14.

The external device 14 can be a portable device to provide feedback related to the recorded signals. In some instances, the external device 14 can be a mobile phone or another device that is approximately the size of a mobile phone (e.g., a PDA, a tablet computing device, or the like). In some instances, the external device 14 can include a display that can provide a graphical representation of the feedback. Additionally, the external device 14 can include a memory and/or a processor to facilitate operations of the external device 14.

The external device 14 can include its own transceiver 26 to receive the amplified signal according to the protocol used by transceiver 24 of the wearable device 12. The external device 14 can also include an analysis component 28 to perform analysis tasks on the recorded signal. For example, the analysis can be related to a state of the brain activity represented by the recorded signals. The state of the brain activity in an epileptic patient can be, for example, hyperexcitability, imminent epileptic seizure, epileptic seizure in progress, rapid eye movement (REM) sleep. As another example, the analysis can include automated seizure detection, seizure counting, seizure duration detection, interictal spike detection, and/or interictal spike counting for the epileptic patient, which is superior to traditional self-reporting. The feedback can include an output related to the state of the brain and/or the automated seizure detection, seizure counting, seizure duration detection, interictal spike detection, and/or interictal spike counting.

The external device 14 can include another transceiver 32 configured to communicate according to a long-range wireless protocol, such as WiFi. The other transceiver 32 can communicate with a remote server 16 to transmit information, including at least one of the recorded data and the corresponding analysis. In some instances, the remote server 16 can provide at least a portion of the information to a neurologist or other medical professional. As an example, the neurologist or other medical professional can determine the efficacy of anti-epileptic medication or other forms of therapy based on the information.

The external device 14 can also be configured for feedback based on the recorded signals and/or the analysis. In some instances, the feedback can be ascertained by a stimulation component 30 based on the recorded signals and/or the analysis to provide closed loop control. In other instances, the feedback can be received from the remote server to provide open loop control. For example, the feedback can be a stimulation, such as a non-invasive electrical stimulation, a vibration, an audio stimulation, a visual stimulation, or any combination thereof. For example, an electrical stimulation can provide neuromodulation of a portion of the brain and/or one or more cervical nerves through any type of stimulation that can be safely applied through the skin surface (e.g., a DC waveform, an AC waveform, and/or a pulse waveform). In some instances, the external device 14 can signal a stimulator to configure the stimulation and deliver the stimulation to the wearable device 12. However, in other instances, the external device 14 can configure and deliver the stimulation to the wearable device 12.

Additional, examples of various stimulations that can be configured by the external device 14 and delivered to the wearable device 12 are described in paragraphs [0012]-

[0030] and [0036]-[0040] of U.S. patent application Ser. No. 14/683,197, which has been incorporated by reference herein.

IV. Methods

Figure 4:
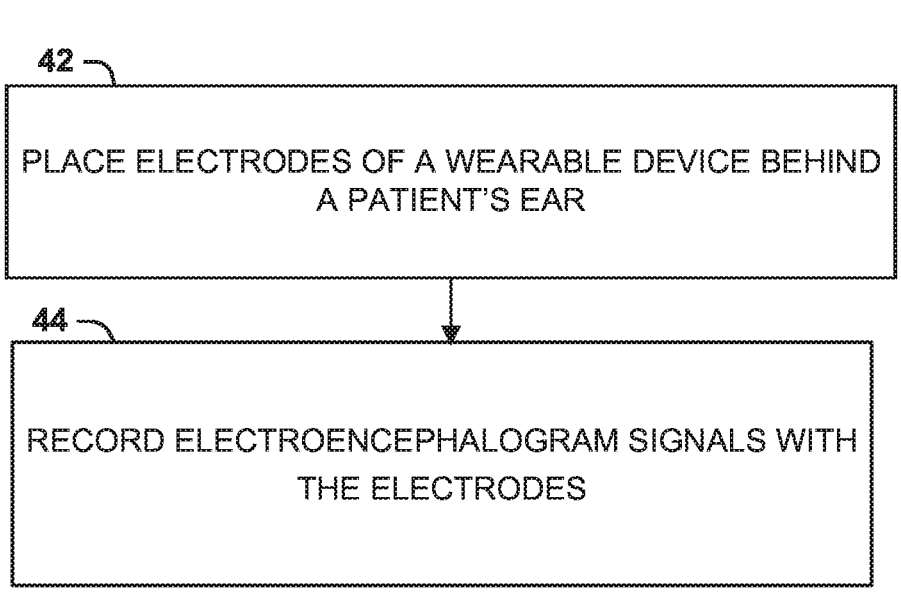
FIG. 4 is a process flow diagram illustrating a method for at home neural recording according to another aspect of the present disclosure.
Figure 5:
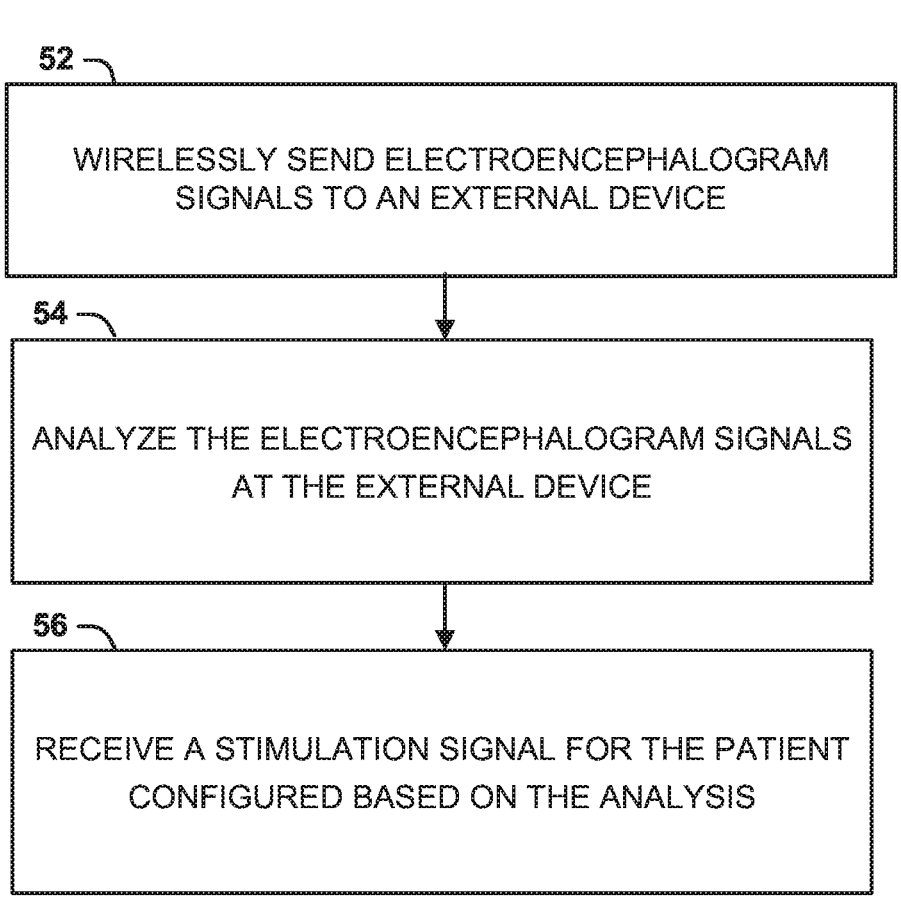
FIG. 5 is a process flow diagram illustrating a method for using the neural recording of FIG. 4.

Another aspect of the present disclosure can include methods that can be used for at home neural recording. FIG. 4 illustrates a method 40 for at home neural recording. FIG. 5 illustrates a method 50 for using the at home neural recording, such as by applying a neural stimulation as feedback to the neural recording. For example, methods 40 and 50 can be executed by the wearable device 12 and the external device 14 of system 10 (shown in FIG. 1).

The methods 40 and 50 are illustrated as process flow diagrams with flowchart illustrations. For purposes of simplicity, the methods 40 and 50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40 and 50.

Referring now to FIG. 4, illustrated is a method 40 for at home neural recording. At step 42, electrodes of a wearable device (e.g., wearable device 12) can be placed behind a patient's ear. The electrodes can include a single electrode (behind one ear), two electrodes (one behind each ear), or more electrodes. In some instances, the wearable device can be configured so that the electrodes are placed in the proper position behind the patient's ear (e.g., over the mastoid process) with minimal effort from the person placing the electrodes. At step 44, electroencephalogram (EEG) signals (or other type of neural recording signals) can be recorded by the electrodes. For example, when two electrodes are used (one behind each ear) a differential recording can be achieved, Referring now to FIG. 5, illustrated is a method 50 for providing feedback related to the EEG signals recorded according to the method 40. At step 52, the EEG signals can be wirelessly transmitted to an external device. For example, the wireless transmission can be according to a short-range transmission protocol. The EEG signals can be processed (e.g., amplified, filtered, or the like) before transmission to the external device. At step 54, the EEG signals are analyzed at the external device. The analysis can include creating a stimulation as feedback for at least a portion of the EEG signals. For example, the EEG signals can be received over time, and the analysis can reveal seizure activity at one of the times. In turn, the external device can configured a stimulation based on the detected seizure activity. At step 56, the stimulation signal for the patient configured based on the analysis can be received from the external device. For example, the stimulation signal can include a vibration, an auditory stimulation, a visual stimulation, and an/or electrical stimulation.

From the above description, those skilled in the art will perceive improvements, changes and modifications. Such improvements, changes and modifications are within the skill of one in the art and are intended to be covered by the appended claims.

The following is claimed:

1. A system comprising:
   a wearable device comprising:
     at least two recording electrodes configured to be placed at predefined locations behind a patient's ear to record an electroencephalogram (EEG) signal, wherein the at least two recording electrodes are arranged in the wearable device at predefined positions corresponding to the at least two predefined locations;
     a reference electrode configured to be placed at another predefined location remote from the patient's ear, wherein the reference electrode is arranged in the wearable device at another predefined position corresponding to the other predefined location;
     an amplifier to amplify the EEG signal;
     a battery; and
     a wireless transmission system to transmit the amplified EEG signal; and
   an external device configured to receive the amplified EEG signal and to perform analysis of the amplified EEG signal.

2. The system of claim 1, wherein the external device is configured to signal a stimulator to provide an electrical stimulation to modulate activity of the brain or one or more cranial nerves based on the amplified EEG signal.

3. The system of claim 2, wherein the electrical stimulation comprises at least one of a direct current (DC) waveform or an alternating current (AC) waveform.

4. The system of claim 2, wherein the electrode is further configured to provide the electrical stimulation.

5. The system of claim 1, wherein the wearable device further comprises another at least one recording electrode configured to be placed behind the patient's other ear to record the EEG signal.

6. The system of claim 1, wherein the electrode is configured to be placed over the mastoid process behind the patient's ear.

7. The system of claim 1, wherein the electrode is configured to be placed on a conductive gel behind the patient's ear.

8. The system of claim 5, wherein the wearable device is configured to release the conductive gel before the electrode is placed behind the patient's ear.

9. The system of claim 1, wherein the at least two recording electrodes are capacitive electrodes.

10. The system of claim 1, wherein the wearable device is configured as earphones, a sleep mask, or eye glasses.

11. The system of claim 1, wherein the external device is a portable computing device configured to communicate with the wireless transmission system to receive the amplified EEG signal.

12. The system of claim 11, wherein the portable computing device is a cellular phone.

13. The system of claim 11, wherein the analysis comprises at least one of seizure detection, seizure counting, seizure duration detection, interictal spike detection, and interictal spike counting.

14. The system of claim 1, wherein the external device sends a signal to the wearable device to provide an acoustic stimulation.

15. The system of claim 1, wherein the external device is configured to communicate wirelessly with a server to provide the amplified EEG signal.

* * * * *